(12) United States Patent
Wyatt

(10) Patent No.: US 7,490,046 B1
(45) Date of Patent: Feb. 10, 2009

(54) METHOD AND SYSTEM FOR MATCHING MEDICAL CONDITION INFORMATION WITH A MEDICAL RESOURCE ON A COMPUTER NETWORK

(75) Inventor: Phil Wyatt, Highland Park, IL (US)

(73) Assignee: Medical Central Online, Lake Forest, IL (US)

( * ) Notice: Subject to any disclaimer, the term of this patent is extended or adjusted under 35 U.S.C. 154(b) by 761 days.

(21) Appl. No.: 09/544,509

(22) Filed: Apr. 6, 2000

(51) Int. Cl.
*G06Q 50/00* (2006.01)

(52) U.S. Cl. .................. 705/2; 705/3; 600/300

(58) Field of Classification Search .......... 705/1, 705/2, 3; 706/45; 707/3, 10; 600/300; 345/700; 379/106.02

See application file for complete search history.

(56) References Cited

U.S. PATENT DOCUMENTS

| | | | |
|---|---|---|---|
| 4,135,241 A | | 1/1979 | Stanis et al. ............. 705/28 |
| 5,619,991 A | * | 4/1997 | Sloane ................. 600/300 |
| 5,652,842 A | | 7/1997 | Siegrist, Jr. et al. ......... 705/2 |
| 5,664,109 A | * | 9/1997 | Johnson et al. ............ 705/2 |
| 5,748,907 A | | 5/1998 | Crane .................... 705/2 |
| 5,805,446 A | | 9/1998 | Hatakeyama et al. ...... 700/28 |
| 5,809,477 A | | 9/1998 | Pollack .................. 705/3 |
| 5,886,693 A | * | 3/1999 | Ho et al. ............... 345/700 |
| 5,911,132 A | * | 6/1999 | Sloane ................... 705/3 |
| 5,974,124 A | * | 10/1999 | Schlueter et al. ...... 379/106.02 |
| 5,997,476 A | * | 12/1999 | Brown ................. 128/920 |
| 6,022,315 A | * | 2/2000 | Iliff ..................... 128/920 |
| 6,199,067 B1 | * | 3/2001 | Geller .................. 707/10 |
| 2003/0177030 A1 | * | 9/2003 | Turner et al. ............. 705/2 |

OTHER PUBLICATIONS

Girishankar, Saroja. Health Care Turns To Web-Based Systems To Remedy Access Ills. Oct. 20, 1997. InternetWeek, p. 20. [Retrieved from Dialog on Sep. 23, 2002], Accession No. 05293926.*
Bazzoli, Fred. Records on the Internet. Feb. 1997, Health Data Management, p. 96. [Retrieved from Dialog on Sep. 23, 2002], Accession No. 04814113.*
Business Wire. "Specialty care Network Announces Internet Strategy; New HealthGrades.com Site to Offer Provider and Health Plan Rating Information." Jun. 30, 1999, Business wire, p. 1519.*

* cited by examiner

*Primary Examiner*—Gerald J O'Connor
*Assistant Examiner*—Natalie A. Pass
(74) *Attorney, Agent, or Firm*—Patents+TMS, P.C.

(57) ABSTRACT

A method and a system for matching medical condition information with medical resources are provided. Specifically, a plurality of medical resources such as, for example, practitioners, specialists, specialty hospitals, or any other medical or extended care providers may have information related thereto stored within a database on a computer network. The information may include information on specific medical conditions, such as, for example, diseases, disorders, or any other medical condition. Alternatively, the medical resource may include information on specific medical procedures in which the medical resource may have a specialty or may otherwise perform. An individual may access a website connected with the database and may enter information on medical conditions and/or medical procedures. A search of the database may then reveal specific medical resource categories and, thence, medical resources that may treat the medical condition or may perform the medical procedures chosen by the individual.

20 Claims, 1 Drawing Sheet

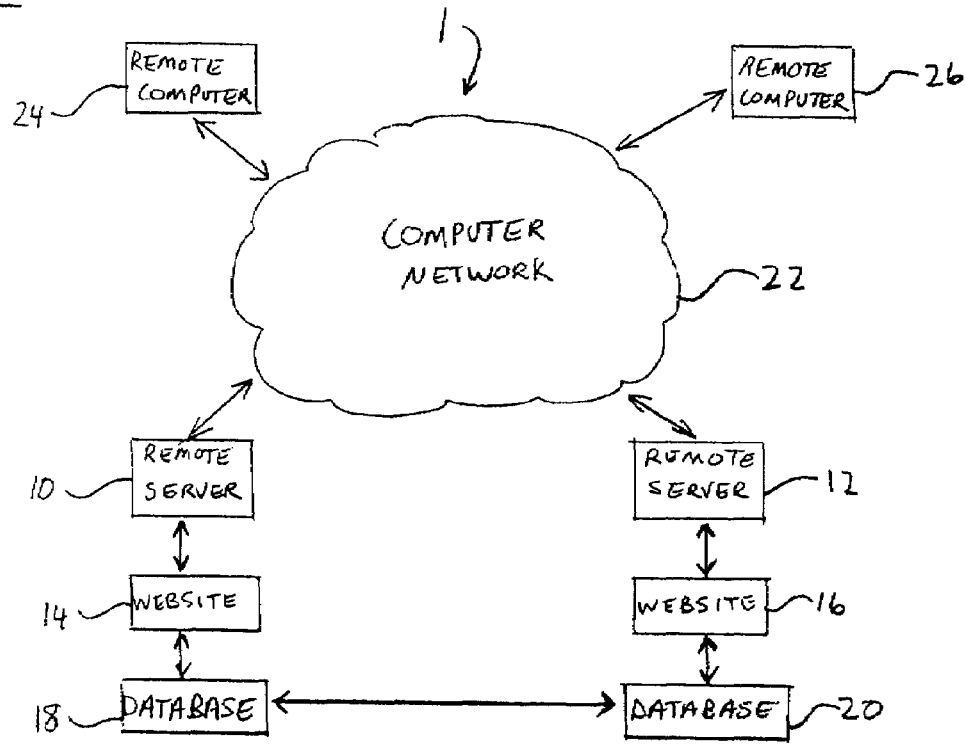
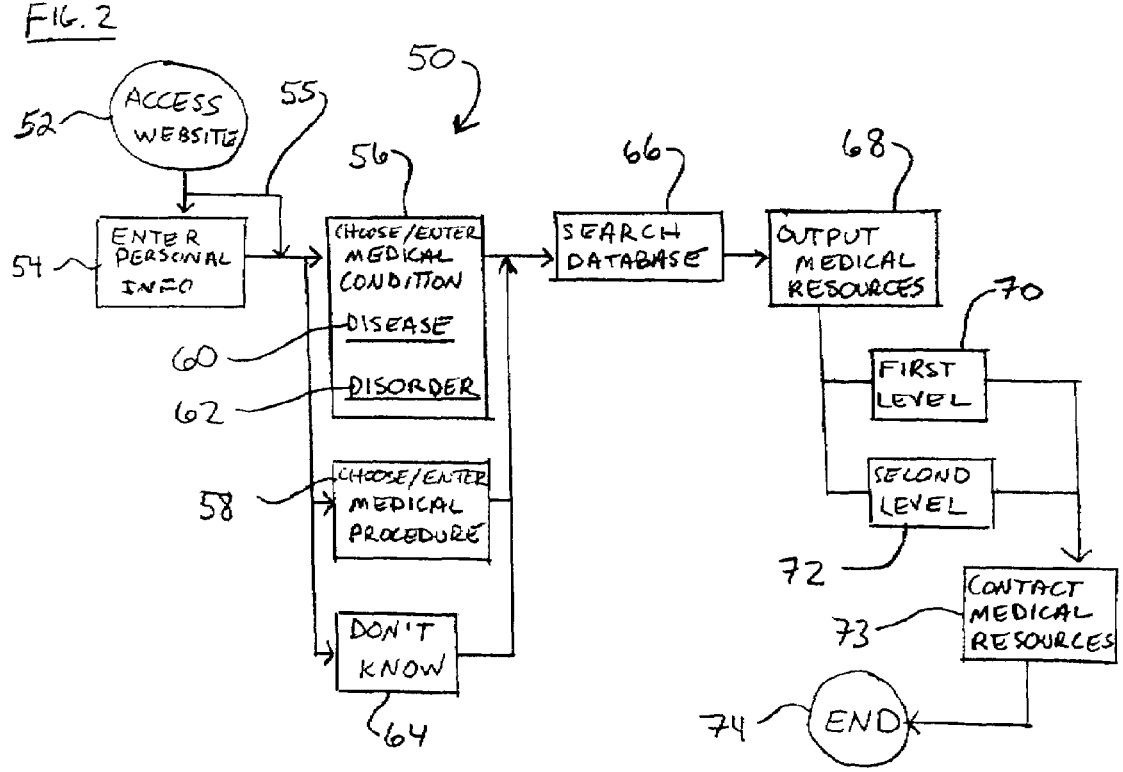

METHOD AND SYSTEM FOR MATCHING MEDICAL CONDITION INFORMATION WITH A MEDICAL RESOURCE ON A COMPUTER NETWORK

BACKGROUND OF THE INVENTION

The present invention generally relates to a method and a system for matching medical condition information with a medical resource. More specifically, the present invention relates to a method and a system for matching medical condition information such as, for example, diseases, disorders and/or medical procedures related thereto with a medical resource that may include, for example, a medical specialist, a specialty hospital and/or any other medical or health facility that may treat the medical condition or that may provide the medical procedure. In addition, the method and the system may be contained on a computer network for an individual to access on a remote computer via the computer network.

It is, of course, generally known to provide information on a computer network. Generally, the computer network may consist of one or a plurality of remote servers that may host one or more websites that may allow an individual to access a database. The database may contain the information in an organized manner so that an individual on a remote computer may access the website and search the database for particular information. The computer network may be a global computer network such as, for example, the internet. Alternatively, the computer network may be contained on an intranet such as a LAN network within an organization, such as a business. An individual may use a search engine to search the contents of the database to retrieve specific information related to a particular query.

Further, it is also generally known to provide access to databases that may contain medical information such as, for example, diseases, disorders or medical procedures. An individual may access the information when the individual wishes to learn more about a particular disease, disorder, and/or medical procedure. This information may be useful if an individual has been diagnosed with the disease or disorder and/or must have a particular medical procedure performed. The information may inform the individual about the particular medical condition.

Moreover, it is also generally known to access information regarding a particular resource related to a subject in which an individual may have an interest. Specifically, an individual may wish to contact the resource and to retrieve the contact information from the computer network.

However, these databases do not allow an individual to download or otherwise retrieve information regarding a particular medical condition and allow the individual to enter further information regarding the individual or the individual's condition. Further, known databases do not match a medical resource with the medical condition so that the individual may contact the medical resource. An individual may desire retrieving further information about the medical condition or otherwise contact the medical resource to set up an appointment.

A need, therefore, exists for an improved method and a system for matching medical condition information with a medical resource on a computer network.

SUMMARY OF THE INVENTION

The present invention generally relates to a method and a system for matching medical condition information with a category of medical resources and, thence, to a specific medical resource. Specifically, the invention relates to a method and a system for matching medical condition information such as, for example, diseases, disorders and/or medical procedures related thereto with a medical resource. The medical resource may include specialists, specialty hospitals and/or any other medical and/or health facility that may treat the designated disease or disorder or may perform specific medical procedures.

To this end, in an embodiment of the present invention, a method for matching medical condition information with a medical resource is provided. The method comprises the steps of: providing a computer network having a plurality of remote computers and at least one remote server wherein the remote server hosts a website; accessing the website via an individual remote computer on the computer network; inputting a query into the website wherein the query relates to a medical condition or selecting from common medical nomenclatures such as ICD-9, ICD-10, SnoMed™, or any other medical nomenclatures that may be apparent to those skilled in the art; providing a database on the remote server wherein the database stores information relating to a plurality of medical conditions; and searching the database for the information wherein the search is based on the query input into or item chosen in a "pick list" from the database and further wherein the search discloses a medical resource that treats the medical condition queried.

In an embodiment, the information is output to the individual remote computer.

In an embodiment, the medical disorders relate to diseases.

In an embodiment, medical procedure information is provided to one of the computers.

In an embodiment, searching the database for medical procedure information is provided.

In an embodiment, a category of potential medical practitioners or facilities is provided.

In an embodiment, a practitioner is disclosed to one of the remote computers that treats the medical condition queried.

In an embodiment, a medical facility is disclosed to the individual remote computer that treats the medical condition queried.

In an embodiment, specific medical resource information is disclosed wherein the specific medical resource information includes a name of the medical resource, a location, contact information and services offered.

In an embodiment, one of the remote computers is linked to a specific website relating to the medical resource.

In an embodiment, the information discloses a plurality of medical resources that treat the medical condition queried.

In an embodiment, the query includes identifying information of an individual using the website wherein search results disclosing a medical resource match the identifying information to the medical resource.

In an embodiment, a plurality of medical resources that treat the disorder queried is disclosed, and the medical resources are ranked based on how the medical resources match the query.

In an embodiment, a plurality of websites on the computer network is provided. Any of the websites may be accessed via the remote computer. The database may be searched via any of the websites.

In an embodiment, a plurality of databases is provided on a plurality of remote servers wherein the databases store the information relating to the medical conditions. The databases are linked via the computer network and the databases are searched for the information.

In another embodiment of the present invention, a system is provided for matching medical condition information with a medical resource. The system has a computer network having a plurality of remote computers and at least one remote server wherein the remote server hosts a website. A database is connected to the remote server wherein the database stores information relating to a plurality of medical conditions. Means is provided for querying the database wherein the query relates to one of the medical conditions. Further, means is provided for searching the database for the information wherein the search is based on the query of the database and further wherein the information discloses a medical resource that treats the medical condition queried.

In an embodiment, means is provided for outputting the information from an individual remote computer.

In an embodiment, the medical conditions relate to diseases.

In an embodiment, a category of potential medical practitioners or facilities is provided.

In an embodiment, the information relating to the medical conditions further relates to medical procedures.

In an embodiment, the information relates to practitioners that treat the medical condition queried.

In an embodiment, a link is provided on the website wherein the link links one of the remote computers to another website providing further information relating to the medical resource.

It is, therefore, an advantage of the present invention to provide a method and a system for matching medical condition information with a medical resource that is accessed via a computer network.

Further, an advantage of the present invention is to provide a method and a system for matching medical condition information with a medical resource category and, thence, a medical resource that provide contact information for the medical resources.

Moreover, an advantage of the present invention is to provide a method and a system for matching medical condition information with a medical resource that allow inputting of individual information to improving matching of a medical resource with the individual.

And, an advantage of the present invention is to provide a method and a system for matching medical condition information with a medical resource that include a database having a plurality of diseases, disorders and medical procedures stored therein for accessing by a remote computer on the computer network.

Still further, an advantage of the present invention is to provide a method and a system for matching medical condition information with a medical resource that allow an individual to enter the specific medical condition or medical procedure to retrieve the information from the database or to allow the individual to choose the specific medical condition or medical procedure via lists stored on the database.

Additional features and advantages of the present invention are described in, and will be apparent from, the detailed description of the presently preferred embodiments and from the drawings.

BRIEF DESCRIPTION OF THE DRAWINGS

FIG. 1 illustrates a network contained between remote servers and remote computers in an embodiment of the present invention.

FIG. 2 illustrates a black box flow diagram illustrating a method for accessing a website and retrieving information therefrom in an embodiment of the present invention.

DETAILED DESCRIPTION OF THE PRESENTLY PREFERRED EMBODIMENTS

The present invention relates to a method and a system for matching medical condition information with a medical resource. More specifically, the present invention relates to a method and a system for matching medical condition information such as, for example, diseases, disorders and/or medical procedures related thereto, with a medical resource such as, for example, specialists, specialty hospitals, and/or any other medical resource. Further, the present invention relates to a method and a system for matching medical condition information with a medical resource contained on a computer network.

Referring now to the drawings wherein like numerals refer to like parts, FIG. 1 illustrates a system 1 that may include a plurality of remote servers 10,12. Contained on the remote servers 10,12 may be websites 14,16, respectively. Each of the websites 14,16 may be connected with databases 18,20, respectively, that may contain information related to a plurality of medical conditions and medical resources that may treat the medical conditions. The databases 18,20 may be connected so that the remote servers 10,12 may access either of the databases 18,20 at any time. The remote servers 10,12 may be incorporated within a computer network 22.

It should be noted that a plurality of remote servers may be included having a plurality of websites. Each website may have a database connected thereto. Therefore, this invention should not be construed as limited to the two remote servers 10,12 as specified herein but merely illustrates that a number of remote servers may be utilized in the computer network. Alternatively, only one remote server containing a website and a database may be used to store the information and to provide access to the database.

The remote servers 10,12 may be connected via the computer network 22. The computer network 22 may be a global computer network such as, for example, the internet or may be an intranet such as, for example, a LAN network that may be contained within a business or other entity. Remote computers 24,26 may be connected with the computer network 22 allowing an individual to access the remote servers 10,12 thereby accessing one of the websites 14,16. Of course, any number of remote computers may be used to access the websites 14,16, and the invention should not be limited as herein described.

Any of the remote computers 24,26 or any other remote computer utilized in the system 1 may be a wireless computer whereby the network 22 may be accessed from a remote location. For example, any of the computers 24,26 may be a Palm Pilot™ device by 3Com, Inc. that may access the internet wirelessly. Further, the computer 24,26 may be a wireless telephone having accessibility to the internet.

FIG. 2 illustrates a method 50 for accessing a website and retrieving information from one of the databases 18, 20, as illustrated in FIG. 1. The method 50 may include an access website step 52. An individual using one of the remote computers 24, 26, as shown in FIG. 1, or any other remote computer connected with the computer network 22 may access one of the websites 14, 16 or any other website that may provide access to databases 18, 20 (shown in FIG. 1), or any other database containing the information therein.

After an individual has accessed the website via the step 52, the individual may enter personal information via a step 54 such as, for example, name, location, and/or contact information or any other information that may be apparent to those skilled in the art. Alternatively, the individual may forego entering personal information via a step 55 for the sake of privacy or for any other reason that may be apparent to those skilled in the art.

After an individual has entered personal information or has decided to skip entering personal information, the individual may choose or otherwise enter a particular medical condition via a step 56 or may choose or otherwise enter a particular medical procedure via a step 58. The medical conditions may be stored within the databases 18,20, or any other database, and may include information relating to diseases 60, disorders 62 or any other medical condition that may be apparent to those skilled in the art and stored within the databases 18,20. The individual may choose the particular medical condition for any number of reasons, such as, for example, because the individual has been diagnosed with a particular disease or disorder or the individual knows someone who has been diagnosed with a particular disease or disorder. The individual may desire to obtain information regarding medical resources that may treat the particular disease or disorder or otherwise specialize in the treatment thereof.

Similarly, the individual may choose a particular medical procedure for any number of reasons, such as, for example, because the individual or someone the individual knows may be undergoing a particular medical procedure and the individual wishes to obtain information on a medical resource that performs the particular medical procedure. Of course, an individual may wish to obtain information relating to medical conditions or medical procedures for any number of reasons that may be apparent to those skilled in the art.

The particular medical conditions may be stored within the databases 18,20, or any other database, and may include information on the diseases 60 and/or the disorders 62. For example, the diseases 60 and/or the disorders 62 may be taken from, or otherwise derived from, the International Code of Diseases (ICD) published by the World Health Organization. Specifically, the diseases 60 and/or the disorders 62 may be taken from ICD-9 or ICD-10 lists or may be taken from SnoMed™. However, any disease or other disorder nomenclature presently known or subsequently developed may be used, and the present invention should not be limited as herein described.

Further, the medical procedures that may be stored within the databases 18,20, or any other databases, may provide information relating to the particular medical procedures, such as, for example, steps in the procedures, risks related to the procedures, or any other information that may be apparent to those skilled in the art and that may inform an individual about a particular medical procedure. After an individual has chosen a medical procedure from one of the databases 18,20, the information related thereto may appear to the individual on the particular remote computer 24,26.

Alternatively, if an individual does not know the medical condition or medical procedure about which information is desired, the individual may choose to browse a list of medical conditions or medical procedures via the "DON'T KNOW" step 64. The don't know step 64 may allow a user to press or activate a don't know button on the website 14,16 and may provide a list of conditions or procedures through which the individual may browse.

After an individual has chosen a particular medical condition or a medical procedure via steps 56 or 58, respectively, the individual may search the database 18,20 via a step 66. The database 18,20 may contain information related to medical resources such as, for example, medical specialists, specialty hospitals or any other medical or health facility that may treat designated diseases 60 or disorders 62 or otherwise perform specific medical procedures. The search of the database 66 may match the medical resources with the particular medical conditions and/or medical procedures chosen by the individual.

The particular medical resources that match the medical conditions and/or medical procedures designated by the individual may be output via a step 68 to the remote computer 24,26 or any other remote computer that is being used by the individual. The medical resources may be output via step 68 in a plurality of different ways. For example, the medical resources may be matched with the medical conditions and/or medical procedures and may be designated as first level or second level as illustrated in steps 70 and 72, respectively. The first level of resources designated at the step 70 may be output first and may contain information relating to general practitioners that may be consulted regarding the particular medical condition and/or medical procedure. Next, the second level of medical resources designated at the step 72 may be output. The second level of medical resources designated at the step 72 may contain information relating to specialists or specialty hospitals that may treat the particular medical condition and/or perform the particular medical procedure.

In addition, the medical resources may be matched with the personal information entered by the individual via the step 54. The medical resources may be listed based on proximity to the individual or whether the medical resource is listed in an individual's insurance plan or for any other reason apparent to those skilled in the art.

Further, the output of medical resources may provide contact information whereby an individual may contact the medical resources via the step 73. For example, name, address and telephone information may be provided. Also, an e-mail address may be provided so the individual may make direct contact with the medical resources. After the medical resources have been output via the step 68 the individual may terminate his or her session with the website 14,16 or any other website via an end step 74. Alternatively, the individual may return back to any of the steps to clarify any information or choose a different medical condition or procedure to search the database.

Still further, medical practitioners may have websites detailing information regarding the practitioners. On each website may be a button, or a plurality of buttons that may start the process of finding medical resources as shown in FIG. 2. In addition, practitioners may have a button on their websites allowing the practitioners to instantly update the databases 18,20 regarding diseases, disorders and/or procedures that the practitioner may have expertise in.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A method for matching medical condition information with a medical resource, the method comprising the steps of:

providing a computer network having a plurality of remote computers and at least one remote server wherein the remote server hosts a website;

accessing the website via an individual remote computer on the computer network;

inputting a query into the website wherein the query relates to a first medical condition;

providing a database on the remote server wherein the database stores first information relating to a plurality of medical conditions and second information relating to a plurality of medical resources wherein the plurality of medical conditions are diseases and disorders and further wherein the plurality of medical resources are medical specialists, specialty hospitals, medical facilities and health facilities which at least one of the plurality of medical conditions;

searching the first information and the second information in the database based on the query input into the website wherein the medical condition of the query is matched to a second medical condition from the plurality of medical resources in the first information wherein a medical resource from the plurality of medical resources in the second information is matched to the medical condition of the query wherein the medical condition of the query is treatable by the medical resource; and displaying third information via the individual remote computer wherein the third information relates to the second medical condition and further wherein the third information relates to the medical resource which matches the medical condition of the query.

2. The method of claim 1 further comprising the step of: outputting the third information to the individual remote computer.

3. The method of claim 1 wherein the medical conditions relate to diseases.

4. The method of claim 1 further comprising the step of: providing medical procedure information to one of the computers.

5. The method of claim 1 further comprising the step of: searching the database for medical procedure information.

6. The method of claim 1 further comprising the step of: disclosing on one of the remote computers a practitioner that treats the medical condition of the query.

7. The method of claim 1 further comprising the step of: disclosing a medical facility to the individual remote computer wherein the medical facility treats the medical condition of the query.

8. The method of claim 1 further comprising the step of: disclosing medical resource information relating to the medical resource wherein the medical resource information includes a name of the medical resource, a location, contact information and services offered.

9. The method of claim 1 further comprising the step of: linking one of the remote computers to a specific website relating to the medical resource.

10. The method of claim 1 wherein the third information discloses more than one medical resource from the plurality of medical resources that treat the medical condition of the query.

11. The method of claim 1 wherein the query includes identifying information of an individual using the website wherein the third information discloses one of the plurality of medical resources which matches the identifying information.

12. The method of claim 1 further comprising the step of: disclosing medical resources from the plurality of medical resources that treat the medical condition of the query; and ranking the medical resources based on how the medical resources match the query.

13. The method of claim 1 further comprising the step of: providing a plurality of websites on the computer network; accessing any one of the plurality of websites via the remote computer; and
searching the database via any one of the plurality of websites.

14. The method of claim 1 further comprising the step of: providing a plurality of databases on a plurality of remote servers wherein the databases store the first information relating to the plurality of medical conditions;
linking the databases via the computer network; and
searching the databases for the third information.

15. A system for matching a medical condition with a medical resource, the system comprising:
a computer network having a plurality of remote computers and at least one remote server wherein the remote server hosts a website;
a database connected to the remote server wherein the database stores first information relating to a plurality of medical conditions and a plurality of medical resources wherein the plurality of medical conditions are diseases and disorders and further wherein the plurality of medical resources are medical specialists, specialty hospitals, medical facilities and health facilities which treat at least one of the plurality of medical conditions;
means for inputting a query wherein the query relates to one of the plurality of medical conditions; and
means for searching the first information in the database based on the query wherein the means for searching matches a medical resource from the plurality of medical resources to the query wherein the medical resource treats one of the plurality of medical conditions of the query;
means for disclosing second information wherein the second information relates to one of the plurality of medical conditions of the query; and
means for contacting the medical resource on the website wherein the medical resource is contactable from the website via the means for contacting the medical resource.

16. The system of claim 15 further comprising:
means for outputting the second information from an individual remote computer.

17. The system of claim 15 wherein the medical conditions relate to diseases.

18. The system of claim 15 wherein the first information relating to the medical conditions further relates to medical procedures.

19. The system of claim 15 wherein the first information relates to practitioners that treat one of the plurality of medical conditions of the query.

20. The system of claim 15 further comprising:
a link on the website wherein the link links one of the remote computers to another website providing third information relating to the medical resource.

* * * * *